United States Patent
Boutoussov

(10) Patent No.: US 7,575,381 B2
(45) Date of Patent: *Aug. 18, 2009

(54) FIBER TIP DETECTOR APPARATUS AND RELATED METHODS

(75) Inventor: Dmitri Boutoussov, Dane Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/904,801

(22) Filed: Sep. 27, 2007

(65) Prior Publication Data

US 2008/0025675 A1   Jan. 31, 2008

Related U.S. Application Data

(62) Division of application No. 11/181,373, filed on Jul. 13, 2005, now Pat. No. 7,290,940.

(51) Int. Cl.
G02B 6/36 (2006.01)
G02B 6/42 (2006.01)

(52) U.S. Cl. .......................................... 385/89; 385/88

(58) Field of Classification Search ........................ None
See application file for complete search history.

(56) References Cited

U.S. PATENT DOCUMENTS

| | | | |
|---|---|---|---|
| 3,831,017 A | 8/1974 | Auer | |
| 4,722,337 A * | 2/1988 | Losch et al. ................... | 606/16 |
| 5,333,221 A | 7/1994 | Briggs et al. | |
| 5,353,147 A * | 10/1994 | Grimes ......................... | 398/28 |
| 5,394,503 A | 2/1995 | Dietz et al. | |
| 5,444,664 A * | 8/1995 | Kuroda et al. ................ | 365/226 |
| 5,540,683 A | 7/1996 | Ichikawa et al. | |
| 5,742,718 A * | 4/1998 | Harman et al. ................ | 385/53 |
| 6,109,797 A | 8/2000 | Nagura et al. | |
| 6,293,706 B1 | 9/2001 | Strike et al. | |
| 6,464,689 B1 | 10/2002 | Qin et al. | |
| 6,829,427 B1 | 12/2004 | Becker | |
| 7,029,185 B2 | 4/2006 | Iwai | |
| 7,123,810 B2 | 10/2006 | Parrish | |

(Continued)

FOREIGN PATENT DOCUMENTS

DE    4026452 A1    3/1992

(Continued)

OTHER PUBLICATIONS

International Search Report, Dec. 1, 2006, PCT/US05/24856.

(Continued)

*Primary Examiner*—Omar Rojas
(74) *Attorney, Agent, or Firm*—Stout, Uxa, Buyan & Mullins, LLP

(57) ABSTRACT

A system and method are described for controlling acceptance of a fiber connector. A configurable adapter is employed for connecting fiber connectors to a laser housing. A specific version of the adapter permits connecting both first- or general-purpose and second- or specific-purpose fiber connectors to the laser housing. A less versatile configuration of the adapter permits connecting first- or general-purpose fiber connectors to the laser housing, but rejects second- or specific-purpose fiber connectors.

8 Claims, 3 Drawing Sheets

U.S. PATENT DOCUMENTS 7,290,940 B2 * 11/2007 Boutoussov ................ 385/53

FOREIGN PATENT DOCUMENTS

| DE | 19510939 A1 | 9/1996 |
| EP | 0654251 A | 5/1995 |
| GB | 2369057 | 5/2002 |
| WO | WO 02/098315 | 12/2002 |

OTHER PUBLICATIONS

Written Opinion, Dec. 1, 2006, PCT/US05/24856.
Supplementary European Search Report in European Application EP05776954, Jan. 8, 2008.
Supplementary European Search Report in European Application EP05770977, Dec. 22, 2008.

* cited by examiner

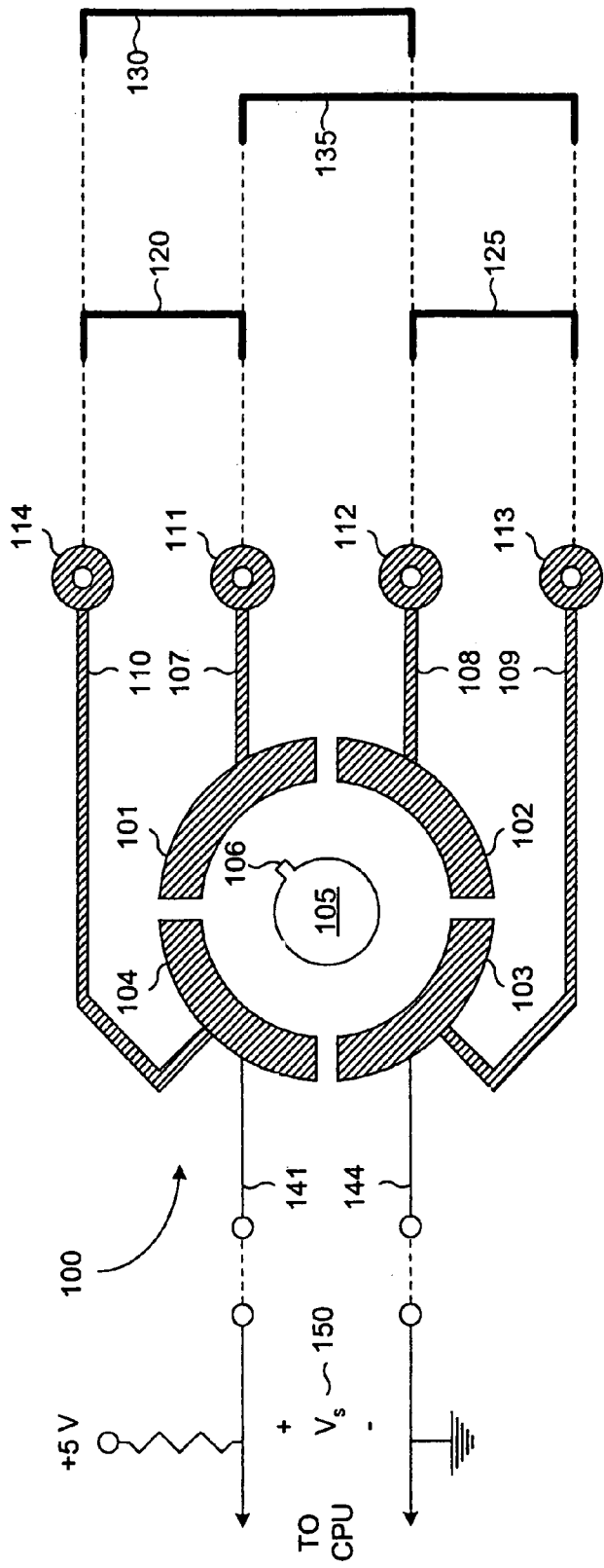
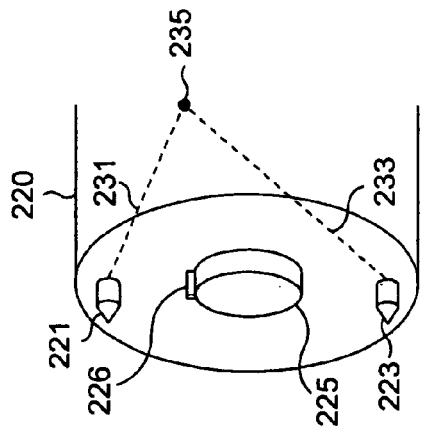
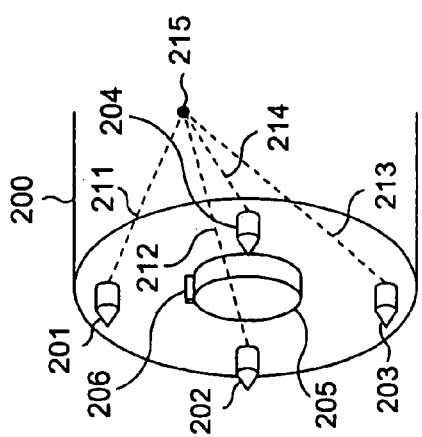
FIG. 2
FIG. 3a
FIG. 3b

FIBER TIP DETECTOR APPARATUS AND RELATED METHODS

CROSS-REFERENCE TO RELATED APPLICATIONS

This application is a divisional of U.S. application Ser. No. 11/181,373, filed Jul. 13, 2005 and entitled FIBER TIP DETECTOR APPARATUS AND RELATED METHODS, now U.S. Pat. No. 7,290,940, the entire contents of which are hereby incorporated by reference. This application relates to U.S. Pat. No. 6,829,427, the entire contents of which are hereby incorporated by reference.

BACKGROUND OF THE INVENTION

1. Field of the Invention

The present invention relates generally to cutting and treatment devices and, more particularly, to housings accommodating different types of waveguides such as fibers and fiber tips.

2. Description of Related Art

Optical cutters are well known in medical, dental, and industrial settings. Generally, optical cutters employ a source of electromagnetic energy, such as a laser source, and an optical fiber system connected to the laser source. The optical fiber system is configured to direct a laser beam through one or more fibers from the laser to a surface to be cut. The optical fiber system may be contained within an optical fiber tube. The optical fiber tube may have a device at an end thereof (a distal end) for controlling delivery of electromagnetic energy to a surface to be cut. Another end (a proximal end) of the optical fiber tube may include a fiber connector for connecting to the laser source, which may be contained within a laser housing.

Fiber tubes may contain one or more optical fibers that differ in certain physical properties. The properties of the fibers and their connectors may be selected according to an application to which the optical cutter is to be applied. For example, optical fibers of a generic medical nature may be selected for general surgical applications. As another example, a specialized fiber and associated connector may serve to operate as a whitening dental handpiece. A fiber used in general medical applications may cost less than a fiber designed for a more specialized or advanced surgical procedure.

A relatively expensive laser source may accommodate an entire group of fibers including both general-purpose and specialized fibers. A relatively less expensive laser source may accommodate only general-purpose fibers.

A need exists for a device capable of differentiating between general-purpose and specialized fibers so that, for example, relatively expensive specialized fibers cannot be used with relatively inexpensive laser sources. A further need exists for a device capable of accepting both general-purpose and specialized fibers.

SUMMARY OF THE INVENTION

The present invention addresses these needs and provides, according to an embodiment, apparatuses and methods for preventing acceptance of a specialized fiber by a relatively inexpensive laser source. An alternative embodiment provides an apparatus and method for accepting both first- or general-purpose fibers and second or specialized fibers.

According to an implementation, the present invention may comprise a method of accepting a fiber connector. The implementation may comprise providing an adapter configured in one of a general configuration and a specific configuration. The implementation further comprises accepting a specific-purpose fiber connector when the adapter is configured in the specific configuration. The implementation still further comprises accepting one of a general-purpose fiber connector and a specific-purpose fiber connector when the adapter is configured in the specific configuration. Another implementation of the method comprises rejecting a specific-purpose fiber connector when providing an adapter configured in the general configuration.

The present invention further comprises a system for controlling acceptance of a fiber connector. The system may comprise, according to an embodiment, an adapter capable of being configured in one of a general configuration and a specific configuration. When configured in the general configuration, the adapter is capable of accepting a general-purpose fiber connector. When configured in the specific configuration, the adapter is capable of accepting one of a general-purpose fiber connector and a specific-purpose fiber connector.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE DRAWINGS

FIG. 2 is a pictorial diagram of a portion of an embodiment of an adapter capable of recognizing a pin configuration;

FIG. 3a is a pictorial diagram of a four-pin housing suitable for fibers used in general surgical applications;

FIG. 3b is a pictorial diagram of a two-pin housing suitable for fibers used in special-purpose or advanced applications;

DETAILED DESCRIPTION OF THE INVENTION

Figure 1:
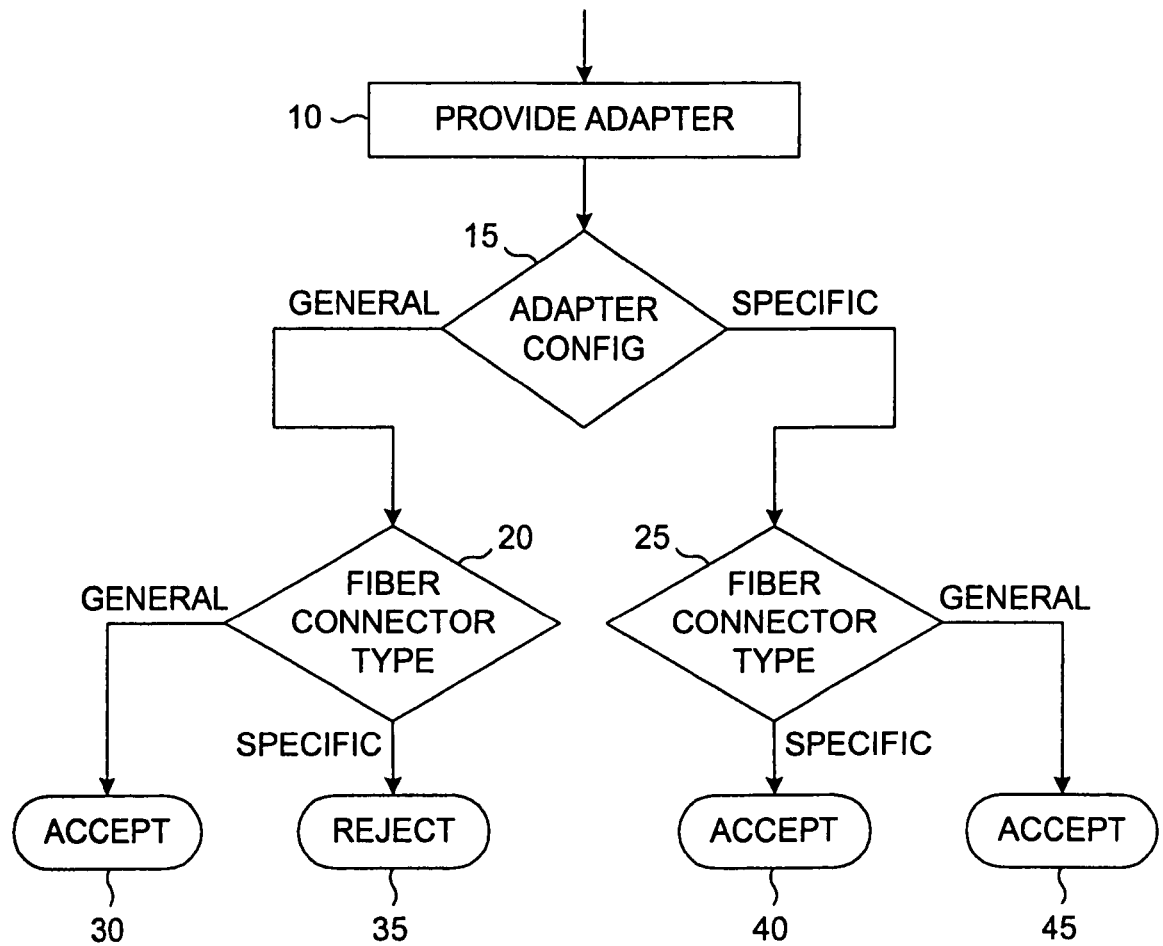
FIG. 1 is a flow diagram illustrating an implementation of a method of the present invention.
Figure 7:
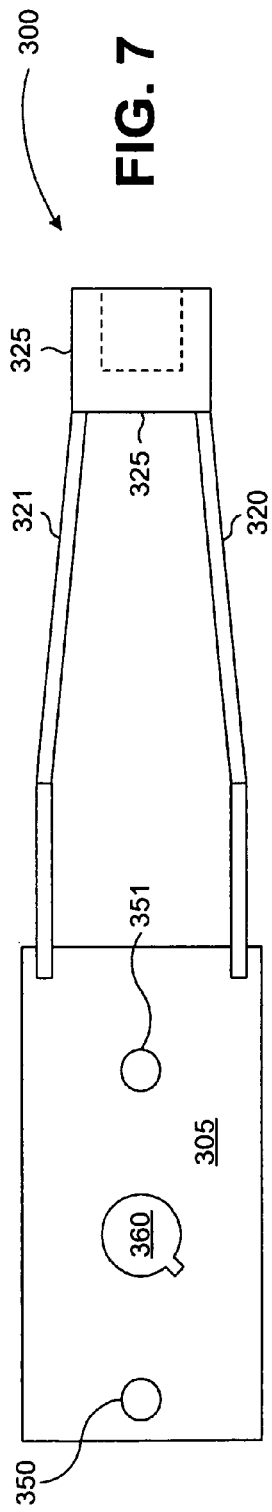
FIG. 7 is a bottom view of the embodiment of the adapter of FIG. 4 configured to connect only fibers used in general surgical applications to a laser housing.

Reference will now be made in detail to embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, northwest, northeast, southeast and southwest may be used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives and equivalents of the embodiments as may fall within the spirit and scope of the invention as defined by the appended claims. It is to be understood and appreciated that the structures described herein do not cover a complete description of, for example, laser housings. The present invention may be practiced in conjunction with various devices and methods that are conventionally used in the art, and only so much of the commonly practiced structures and steps are included herein as are necessary to provide an understanding of the present invention. The present invention has applicability in the field of material removal and treatment devices and processes in general. For illustrative purposes, however, the following description pertains to an embodiment comprising an exemplary device and method for differentiating between general-purpose and specific-purpose fiber connectors.

Although the disclosure herein refers to, for example, a fiber detector apparatus for detecting and providing information about optical fibers connectable to a laser source that is used, for example, to remove material from surfaces, such as biological surfaces, the apparatuses and methods of the present invention are not to be limited to such disclosures. The apparatus may be used to detect waveguides (e.g., fibers) or other attachments in any system where, for example, the physical properties of the waveguides or attachments may be relevant determinants in the general or specific operation or applicability of the system. Additionally, in the case of fibers, other sources of energy may be transmitted through the fibers, and the devices may be used to remove material from various types of surfaces amenable to such procedures. For example, in addition to medical applications, the apparatus may be used in devices that are used to etch material from nonbiological surfaces such as metals or silicon chips. In addition, the apparatus of the invention may be used, for example, in various optical systems that employ waveguides (e.g., optical fibers) for directing energy (e.g., light energy) to a surface to be examined.

Referring more particularly to the drawings, FIG. 1 is a flow diagram illustrating an aspect of a method of the present invention. The illustrated implementation discriminates between first types of attachments, such as general-purpose surgical fiber connectors (referred to as first- or general-purpose fiber connectors) and second types of attachments, such as fiber connectors designed for specialty applications (referred to as second- or specific-purpose fiber connectors). The discrimination may be controlled according to a configuration of an adapter, the adapter being provided at step 10. According to an illustrative embodiment, the adapter may be used to connect a fiber connector to a laser source. As is more particularly described below with reference to FIGS. 3a and 3b, a fiber connector may be formed as a hub comprising a collection of pins that may be arranged in a circle. The adapter may comprise conductive pin-contacting surfaces, which are electrically isolated from each other and which are disposed on a portion of the adapter that makes mechanical contact with the hub. The pins of the fiber connector may make electrical contact with the pin-contacting surfaces of the adapter. For example, the adapter may comprise four conductive pin-contacting surfaces arranged in a circle. In accordance with an aspect of the present invention, mechanical and/or electrical characteristics of the pins of a fiber connector and of the pin-contacting surfaces of the adapter may be designed to enable the adapter to distinguish between general-purpose fiber connectors and specific-purpose fiber connectors.

In an exemplary embodiment, the adapter may be configured in one of a general configuration and a specific configuration. Step 15 of an implementation of the method illustrated in FIG. 1 comprises determining the configuration of the adapter. This determination may be performed, for example, by the laser source. For example, the configuration of the adapter may be determined by the electrical characteristics of the pin-contacting surfaces. If the adapter is configured in a general configuration, another test may be performed at step 20 to determine a type of fiber connector. The determination of the type of fiber connector may be performed, for example, by the adapter and/or laser source. The type of the fiber connector, which may be one of a general-purpose fiber connector and a specific-purpose fiber connector, may be indicated by the mechanical and/or electrical characteristics of the pins placed in the fiber connector. If the fiber connector is a general-purpose fiber connector, then the fiber connector is accepted at step 30. The fiber connector is rejected at step 35 if the fiber connector is a specific-purpose fiber connector when the adapter is configured in a general configuration. If the adapter is configured in a specific configuration, then a test is performed at step 25 to determine the type of fiber connector. A specific-purpose fiber connector is accepted at step 40, and a general-purpose fiber connector also is accepted at step 45.

In a typical embodiment, specific-purpose fiber connectors may be relatively expensive. The invention provides a method by which relatively expensive fiber connectors may be rejected by certain devices. For example, by configuring the adapter in a general (e.g., low-cost) configuration, specific-purpose fiber connectors may not be accepted by the adapter. On the other hand, by configuring the adapter in a specific (e.g., high-cost) configuration, either a general-purpose or a specific-purpose fiber connector may be accepted.

FIG. 2 is a pictorial diagram of a portion of an embodiment of an adapter 100 capable of recognizing a pin configuration. The illustrated embodiment comprises four conductive pin-contacting surfaces 101, 102, 103 and 104 arranged in a circle. For convenience, surface 101 may be referred to as a northeast surface. Similarly, remaining surfaces 102, 103 and 104 may be referred to, respectively, as southeast, southwest and northwest surfaces. The conductive surfaces 101, 102, 103 and 104 are electrically connected by respective electrical connections 107, 108, 109 and 110 to respective nodes or terminal pads 111, 112, 113 and 114. The terminal pads 111, 112, 113 and 114 may be connected in various ways by jumpers 120, 125, 130 and 135 in order to establish a configuration of the adapter 100. For example, jumper 120 may be electrically connected to terminal pads 114 and 111, thereby establishing an electrical connection between the northwest surface 104 and the northeast surface 101. Similarly, jumper 125 may be electrically connected to terminal pads 112 and 113 to establish an electrical connection between the southwest surface 103 and southeast surface 102. As is more particularly described below with reference to FIG. 3b, connecting jumpers 120 and 125 as described may configure the adapter 100 in a specific configuration.

In certain implementations, when no jumpers are connected among terminal pads 111, 112, 113 and 114, the adapter 100 may be said to be configured in a general configuration. According to another embodiment, connecting terminal pads 114 and 112 with a jumper 130 and connecting terminal pads 111 and 113 with another jumper 135 also may configure the adapter 100 in a general configuration.

A pictorial diagram of an embodiment of a general-purpose fiber connector is illustrated in FIG. 3a. The illustrated embodiment comprises a nominally cylindrical housing, which may be a Scale Manufacturers Association (SMA) housing 200, that supports four electrically conductive pins 201, 202, 203 and 204. Each fiber connector can have a laser fiber connected to it capable of receiving laser energy from a laser housing. The electrically conductive pins 201, 202, 203 and 204 in the illustrated embodiment may be electrically connected together with electrical connections 211, 212, 213 and 214 that electrically connect each of the electrically conductive pins 201, 202, 203 and 204 to a common point 215. Alternatively, the SMA housing 200 may be formed of conductive material such as metal that connects electrically conductive pins 201, 202, 203 and 204 together electrically.

The illustrated embodiment further comprises a fiber guide portion 205 on which may be formed an optional key 206. The fiber guide portion 205 may match with an aperture 105 in the adapter 100 (FIG. 2). The general-purpose fiber connector may connect to the adapter 100 in a manner such that the fiber guide portion 205 (FIG. 3a) fits into the aperture 105 (FIG. 2) so that the adapter 100 is aligned (e.g., mechanically aligned) with the general-purpose fiber connector. Additionally, the aperture 105 may have formed therein a notch 106 that mates with the key 206 (FIG. 3a) on the fiber guide portion 205. When the key 206 fits into the notch 106 (FIG. 2), electrically conductive pins 201, 202, 203 and 204 (FIG. 3a) may make electrical contact with the respective conductive pin-contacting surfaces 101, 102, 103 and 104 (FIG. 2).

The fiber guide portion 205 further may have a size matching that of an aperture 360 disposed in a fiber detector printed circuit (PC) board 305 as is more particularly described below with reference to FIGS. 4-7. In modified embodiments, other alignment structures known to those skilled in the art, or no alignment structures at all, may be implemented alone or in combination with one or more of the fiber guide portion 205, key 206, aperture 105, notch 106 and aperture 360. According to one embodiment, a key 206 and notch 106 are not used and an alternative (e.g., optical) structure and protocol are employed, for example, to align the electrically conductive pins 201, 202, 203 and 204 (FIG. 3a) with the conductive pin-contacting surfaces 101, 102, 103 and 104 (FIG. 2).

The embodiment of the portion of the adapter 100 illustrated in FIG. 2 may facilitate acceptance rather than rejection of a general-purpose fiber connector, which has been connected to the adapter 100. For example, with reference to FIG. 2, electrical connections 141 and 144 may connect, respectively, to the northwest surface 104 and the southwest surface 103. Electrical connection 141 may be connected to a 5 V supply voltage and a resistor and/or to a high impedance input of a decision device having, for example, a central processing unit (CPU). Electrical connection 144 further may connect to a ground terminal that, likewise, may be connected to the CPU.

As presently embodied, when no fiber connector is connected to the adapter 100, no electrical path within the adapter 100 connects the electrical connections 141 and 144. Accordingly, a sensed voltage $V_s$ 150 in the illustrated embodiment assumes a value of about 5 V that may be interpreted by the CPU as a high logic state. The CPU may be designed to accept no connector when a high logic state is present. When a general-purpose fiber connector, for example, the general-purpose fiber connector illustrated in FIG. 3a, is connected to the adapter 100, a conducting path is established between electrical connection 141, conducting surface 104, pin 204 (FIG. 3a), electrical connection 214, common point 215, electrical connection 213, pin 203, conducting surface 103 and electrical connection 144. (It should be noted that in this exemplary embodiment the identified conducting path is established regardless of the configuration of jumpers 120, 125, 130 and 135.) Consequently, the sensed voltage $V_s$ 150, becomes essentially zero volts, a value that may be sensed by the CPU as a low logic state. The CPU then may cause the general-purpose fiber connector to be accepted. Accordingly, regardless of the presence or configuration of jumpers 120, 125, 130 and 135, the general purpose fiber connector of FIG. 3a will be accepted by the CPU, which in the present embodiment is configured to accept connectors upon detection of a low logic state.

FIG. 3b is a pictorial diagram of an embodiment of another fiber connector, the illustrated fiber connector being a specific-purpose fiber connector. In contrast to the architecture of the general-purpose fiber connector of FIG. 3a, the illustrated embodiment of FIG. 3b comprises a nominally cylindrical housing, e.g., an SMA housing 220, supporting, not four, but two, electrically conductive pins 221 and 223. Electrically conductive pins 221 and 223 are electrically connected together. For example, electrically conductive pins 221 and 223 may be electrically connected through respective electrical connections 231 and 233 that, themselves, connect at a common point 235. A fiber guide portion 225 and key 226 may facilitate mechanical connection and alignment of the specific-purpose fiber connector with the adapter 100 (FIG. 2) in the same manner as that already described for the general-purpose fiber connector illustrated in FIG. 3a.

Consider, now, what happens when the specific-purpose fiber connector of FIG. 3b is connected to the adapter 100 of FIG. 2 with the adapter 100 configured in the general configuration. First, suppose the adapter 100 is configured with no jumpers 120, 125, 130 and 135 connected. Because of the action of the key 226 and the notch 106, connecting the specific-purpose fiber connector of FIG. 3b to the adapter 100 brings pin 221 into contact (e.g., electrical contact) with conducting surface 101 and, further, brings pin 223 into contact (e.g., electrical contact) with conducting surface 103. It will be appreciated that no conducting path is established between electrical connections 141 and 144 in this example. Similarly, if the adapter 100 is configured with jumpers 130 and 135 connecting, respectively, terminal pads 114 and 112 and terminal pads 111 and 113, it should be noted that, again, no conducting path exists between electrical connections 141 and 144. In both cases the sensing voltage $V_s$ 150 assumes a value of approximately 5V, which may be interpreted by the CPU as a high logic state. Accordingly, the CPU does not accept the specific-purpose fiber connector when the adapter 100 is configured in a general configuration.

The adapter 100 may be configured in a specific configuration by attaching jumper 120 (FIG. 2) to connect terminal pads 114 and 111 and by attaching jumper 125 to connect terminal pads 112 and 113. When the specific-purpose fiber connector of FIG. 3b is connected to the adapter 100, pin 221 again contacts conducting surface 101, and pin 223 again contacts conducting surface 103. Because of the action of jumpers 120 and 125 in this example, a conducting path is established between electrical connections 141 and 144. That is, electrical connection 141 connects to surface 104, which is electrically connected by conducting path 110 to terminal pad 114. Terminal pad 114 is electrically connected through jumper 120 to terminal pad 111, which is connected electrically to surface 101 by conducting path 107. Conducting surface 101 makes electrical contact with pin 221 (FIG. 3b), which is electrically connected to pin 223 through electrical connection 231, common point 235 and electrical connection 233. Pin 223 connects, in turn, to conducting surface 103, which connects to electrical connection 144, thereby completing a conducting path between electrical connection 141 and electrical connection 144. The completed conducting path causes the sensing voltage $V_s$ 150 to become essentially zero, thereby asserting a low logic state that may be sensed by the CPU, which may cause the specific-purpose fiber connector to be accepted.

Similarly, the general-purpose fiber connector illustrated in FIG. 3a is, likewise, accepted by the CPU when the adapter 100 is configured in the specific configuration. That is, for example, electrical connection 141 electrically connects to surface 104, which electrically connects to conducting path 110, which electrically connects to terminal pad 114, which electrically connects to jumper 120, which electrically connects to terminal pad 111, which connects to conducting path 107, which electrically connects to conducting surface 101, which makes electrical contact with pin 201 (FIG. 3a), which electrically connects to electrical connection 211, which electrically connects to common point 215, which electrically connects to electrical connection 213, which electrically connects to pin 203, which makes electrical contact with conducting surface 103, which connects electrically to electrical connection 144. The conducting path just outlined causes the sensing voltage VS 150 to become essentially zero, leading to accepting of the general-purpose fiber connector by the CPU.

It should be appreciated that the combination of the fiber connectors of the types illustrated in FIGS. 3a and 3b and the adapter 100 as illustrated in FIG. 2 comprise a system capable of controlling acceptance by a laser source of a fiber connector. In particular, the system causes specific-purpose (i.e., high-cost) fiber connectors to be rejected when the adapter 100 is configured in the general configuration. The system further causes acceptance of both general-purpose fiber connectors and specific-purpose fiber connectors when the adapter 100 is configured in the special configuration.

Figure 6:
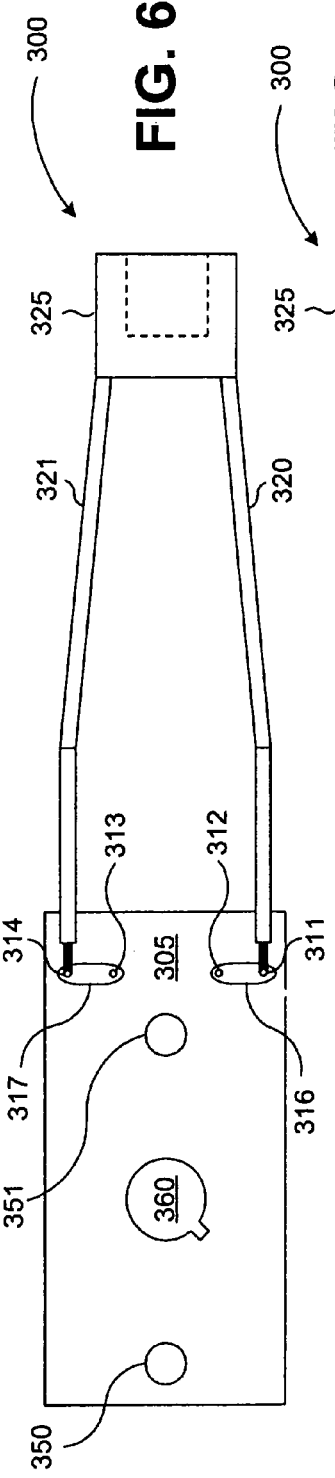
FIG. 6 is a bottom view of the embodiment of the apparatus of FIG. 4 configured to connect either fibers used in general surgical applications or fibers used in advanced applications to a laser housing.
Figure 5:
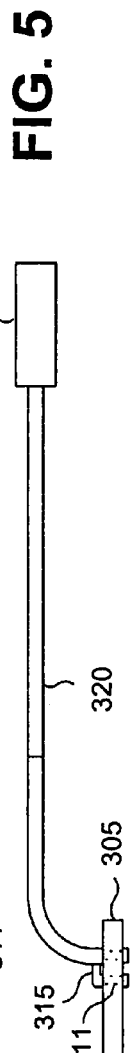
FIG. 5 is a side view of the apparatus of FIG. 4.
Figure 4:
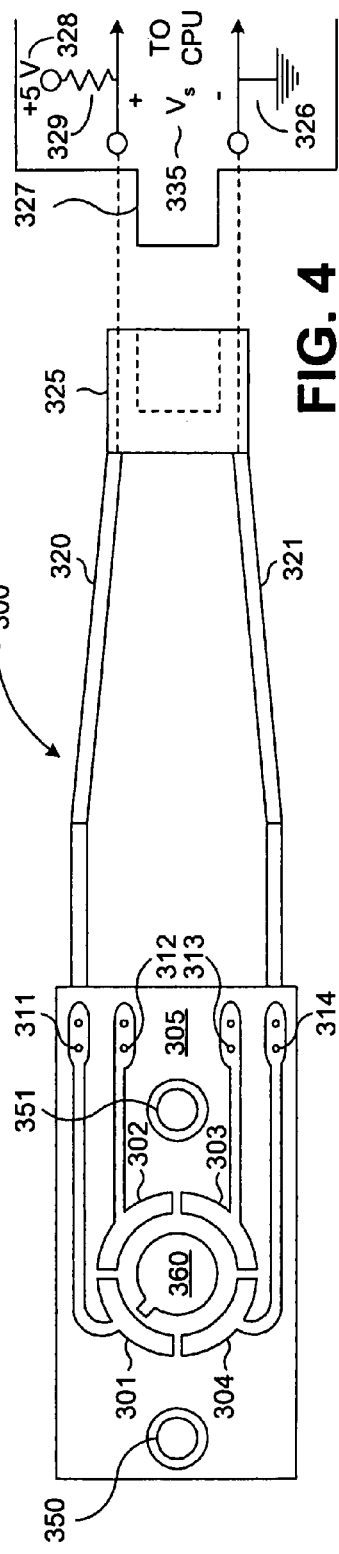
FIG. 4 is a top view of an embodiment of an apparatus suitable for connecting a fiber housing to a laser housing according to the present invention.

FIGS. 4-6 are pictorial diagrams illustrating a portion of an embodiment of a laser housing comprising an apparatus 300 capable of facilitating discrimination between general-purpose and specific-purpose fiber connectors according to the present invention. Connecting the apparatus 300 to a laser housing may effectively characterize the laser housing as a first type (e.g., Version A) of laser housing or as a second type (e.g., Version B) of laser housing. Generally, a Version A laser housing may accommodate both general-purpose and specific-purpose fiber connectors, and a Version B laser housing may accommodate only general-purpose fiber connectors. According to an aspect of the present invention, specific-purpose fiber connectors may comprise (e.g., may be formed, sold or manufactured with) an entire group of fibers, whereas general-purpose fiber connectors may comprise (e.g., may be formed, sold, or manufactured with) only a subgroup of the entire group of fibers, such as fibers of a general surgical nature. In an exemplary embodiment, each fiber connector is provided (e.g., sold or attached) with a fiber, wherein each general-purpose fiber connector may have a general-purpose fiber attached thereto and each specific-purpose fiber connector may have an attachment in the form of a specific-purpose fiber. The apparatus 300, therefore, may be configured (e.g., by adapter 100) to function as a Version A laser housing, thus facilitating accommodation of an entire group of fibers, and to function as a Version B laser housing whereby accommodation of only a subgroup of fibers is facilitated. (A Version B laser housing typically rejects fibers not in the subgroup.) For example, a Version B laser housing may be a less-expensive version that only accommodates fibers of a general surgical nature, whereas a Version A laser housing, which may be more costly, may be constructed to accommodate, in addition to fibers of a general surgical nature, at least an additional part of (and preferably a whole other part of) another (e.g., more specialized, advanced and/or more expensive) collection of fibers in the entire group. An example of one of the fibers that may be accommodated by a Version A laser housing and not accommodated by a Version B laser housing is a whitening fiber connector that operates as a whitening handpiece when used with a Version A laser housing. In this example, both Version A and Version B laser housings may accommodate general surgical fibers.

The embodiment of the apparatus 300 illustrated in FIG. 4 comprises a fiber detector printed circuit board 305 (shown in a top view) that may comprise an SMA receptacle capable of accepting a fiber connector, (cf. FIGS. 3a and 3b) implemented as an SMA housing. The SMA housing may comprise a fiber guide portion 205 (cf. FIG. 3a) constructed to be inserted through an aperture 360 of the fiber detector printed circuit board and, subsequently, into a fiber-guide-receiving aperture (not shown) of an SMA receptacle of the laser housing. The illustrated embodiment of the printed circuit board 305 has formed thereon conducting surfaces circularly arranged in quadrants 301, 302, 303 and 304. The respective quadrants 301, 302, 303 and 304 are connected electrically to terminals 311, 312, 313 and 314 that may pass through the fiber detector printed circuit board 305. Conductive leads 320 and 321 connect terminals 311 and 314 to a female plug 325. Female plug 325 may mechanically connect to male plug 327, thereby electrically connecting conductive lead 320 to a supply voltage, for example, +5 V 328, through a resistor 329. The female plug 325 further may connect conductive lead 320 to an input of a sensing device having, e.g., a CPU, typically disposed within the laser housing. The mechanical connection further connects conductive lead 321 to a ground terminal 326 likewise situated within the laser housing. According to an exemplary embodiment, the fiber detector printed circuit board 305 is mechanically coupled to the laser housing screws (also not shown) passing through apertures 350 and 351.

A sensing device, which may comprise a CPU, in the laser housing may monitor a voltage VS 335 between the conductive leads 320 and 321 when the female plug 325 and the male plug 327 are connected. The CPU may interpret a nominally 5 V value for $V_s$ 335 to represent a high logic state. A nominally zero value for $V_s$ 335 may be interpreted as a low logic state by the CPU. A low logic state detected by the CPU may cause a fiber connector to be accepted as is more particularly described below.

A side view of the embodiment of FIG. 4 is illustrated in FIG. 5 and shows a connection 315 of the conductive lead 320 to terminal 311. A corresponding connection of the conductive lead 321 to terminal 314 is not shown. The connections may be formed using methods well understood in the art. For example, a soldering method may be used.

The apparatus 300 of FIG. 4 is shown in bottom view in FIG. 6, wherein a jumper 316 electrically connects terminal 311 to terminal 312 and another jumper 317 electrically connects terminal 313 to terminal 314. Jumpers similar to jumpers 316 and 317 may be used selectively to configure the apparatus 300 in one of two versions. For example, a relatively more versatile version of the apparatus 300, e.g., a Version A type of apparatus 300, may be capable of accepting either a general-purpose or a specific-purpose fiber connector. A less versatile version, e.g., a Version B type of apparatus 300, may be capable of accepting only a general-purpose fiber connector. A Version B type of apparatus 300, it should be understood, would not accept a specific-purpose fiber connector. According to an exemplary embodiment of the apparatus 300, placing jumper 316 to connect terminals 311 and 312 and placing jumper 317 to connect terminals 313 and 314 configures the apparatus 300 as a Version A type. Another embodiment of the apparatus 300 illustrated in FIG. 7 comprises no jumpers, thereby configuring the apparatus 300 as a Version B type. In an alternative embodiment (not illustrated) the apparatus 300 is configured as a Version B type by employing a first jumper to connect terminal 311 to terminal 313 and a second jumper to connect terminal 312 to terminal 314.

The apparatus 300 illustrated in FIGS. 4 and 6 may be employed in conjunction with fiber connectors similar to those illustrated in FIGS. 3a and 3b. In particular, a general-purpose fiber connector as illustrated in FIG. 3a may be connected to the apparatus 300 of FIG. 4 with the fiber guide portion 205 and (optionally) a key 206 oriented to mate with a matching aperture (optionally, comprising a notch) 360 on the fiber detector printed circuit board 305. When so oriented, electrically conductive pins 201, 202, 203 and 204 on the connector of FIG. 3a may make electrical contact with, respectively, quadrants 301, 302, 303 and 304 on the fiber detector printed circuit board 305 of FIG. 4. With the apparatus 300 configured as a Version A type (for example, with jumper 316 connecting terminal 311 to terminal 312 and with jumper 317 connecting terminals 313 and 314 as illustrated in FIG. 6), a conducting path is formed, for example, by conductive lead 320, terminal 311, quadrant 301, pin 201 (FIG. 3a), electrical connection 211, common point 215, electrical connection 214, pin 204, quadrant 304 (FIG. 4), terminal 314 and conductive lead 321. When female plug 325 is connected to male plug 327 (FIG. 4), the conducting path causes a sensed voltage $V_s$ 335 to be essentially zero, a condition that may be interpreted by the CPU as a low logic state thus causing a laser housing having connected thereto a Version A type of apparatus 300 (i.e., a Version A laser housing) to accept the general-purpose fiber connector. Further, a Version A type of apparatus 300 is capable of accepting a specific-purpose fiber connector. To demonstrate, with a specific-purpose fiber connector as illustrated in FIG. 3b connected to the apparatus 300 of FIG. 4, the apparatus 300 being configured as a Version A type, pin 221 (FIG. 3b) makes electrical contact with quadrant 301 (FIG. 4), and pin 223 makes electrical contact with quadrant 303 (FIG. 4) when the fiber guide portion 225 and key 226 (FIG. 3b) are mechanically mated with the aperture and notch 360 (FIG. 4) of the fiber detector printed circuit board 305. In this instance, a conducting path is formed by conductive lead 320, terminal 311, quadrant 301, pin 221 (FIG. 3b), electrical connection 231, common point 235, electrical connection 233, pin 223, quadrant 303, terminal 313, jumper 317 (FIG. 6), terminal 314 and conductive lead 321. Connecting female plug 325 to male plug 327 again causes the sensed voltage $V_s$ 335 to be essentially zero. The CPU may interpret the essentially zero voltage as a low logic state and may cause the laser housing to accept the specific-purpose fiber connector when the apparatus 300 is configured as a Version A type.

When the apparatus 300 is configured as a Version B type, a general-purpose fiber connector as illustrated in FIG. 3a may be accepted, but a specific-purpose fiber connector as illustrated in FIG. 3b may be rejected by a laser housing having connected thereto a Version B type of apparatus 300. Consider, for example, connecting a general-purpose fiber connector of the a illustrated in FIG. 3a to the apparatus 300 as already described wherein the apparatus 300 is configured as a Version B type. In particular, assume that no jumpers connect any of terminals 311, 312, 313 and 314 to any other of the same terminals 311, 312, 313 and 314. A conductive path is formed in this case between conductive lead 320 and conductive lead 321, for example, as follows. Conductive lead 320 connects to terminal 311, which connects to quadrant 301, which contacts pin 201 (FIG. 3a), which connects to electrical connection 211, which connects to common point 215, which connects to electrical connection 214, which connects to pin 204, which makes contact with quadrant 304, which connects to terminal 314, which connects to conducting lead 321. Accordingly, when female plug 325 connects to male plug 327, sensed voltage $V_s$ 335 becomes essentially zero, and the general-purpose connector is accepted as already described. Conversely, when the specific-purpose fiber connector (FIG. 3b) connects to the Version B type of apparatus 300, no conductive path is formed, sensed voltage $V_s$ 335 maintains a value interpreted by the CPU as a high logic state, and the specific-purpose fiber connector (FIG. 3b) is not accepted.

Summarizing, when a two-pin fiber connector (cf. FIG. 3b) is coupled to a Version B laser housing, the two pins 221 and 223 contact quadrants 301 and 303. In embodiments wherein a second key is disposed on the fiber guide portion 205 opposite to key 206, the two pins 221 and 223 may contact either quadrants 301 and 303 or quadrants 303 and 301, respectively. In embodiments wherein no key 206 is used, the two pins 221 and 223 may contact quadrants 301 and 303, quadrants 303 and 301, quadrants 302 and 304, or quadrants 304 and 302. In any of these cases, quadrants 301 and 304 are not electrically connected, so that the laser housing will not accept the two-pin fiber connector.

According to certain aspects of the present invention, varying, similar, or identical laser housings may be configured as either Version A laser housings or Version B laser housings simply by coupling female plug 325 (FIG. 4) of a corresponding a Version A type of apparatus 300 (FIGS. 4-6) or a Version B type of apparatus 300 (FIG. 7) to male plug 327 (FIG. 4). As already described, a fiber detector printed circuit board of an apparatus 300 configured as a Version A type or a Version B type may be mechanically coupled to a laser housing with screws inserted through apertures 350 and 351. A user (e.g., a customer), therefore, can purchase a Version A laser housing or a Version B laser housing and can further purchase/obtain various fibers connected to fiber connectors adapted to be connected to the laser housings. That is, since only four-pin fiber connectors can be used with a Version B laser housing in the illustrated embodiment, two-pin fibers (i.e., two pin fiber connectors) would be rejected by a laser housing unless, for example, a customer or user were to upgrade to a Version A laser housing. For instance, having already purchased a Version B laser, the customer may subsequently be presented with an option to pay an additional sum and upgrade his or her housing to function as a Version A laser. Upgrading may be accomplished by replacing a Version B laser housing with a laser housing incorporating a Version A type of apparatus 300.

Corresponding or related structure and methods described in the following patents assigned to BioLase Technology, Inc., are incorporated herein by reference in their entireties, wherein such incorporation includes corresponding or related structure (and modifications thereof) in the following patents which may be (i) operable with, (ii) modified by one skilled in the art to be operable with, and/or (iii) implemented/used with or in combination with any part(s) of, the present invention according to this disclosure, that/those of the patents, and the knowledge and judgment of one skilled in the art: U.S. Pat. No. 5,741,247; U.S. Pat. No. 5,785,521; U.S. Pat. No. 5,968,037; U.S. Pat. No. 6,086,367; U.S. Pat. No. 6,231,567; U.S. Pat. No. 6,254,597; U.S. Pat. No. 6,288,499; U.S. Pat. No. 6,350,123; U.S. Pat. No. 6,389,193; U.S. Pat. No. 6,544,256; U.S. Pat. No. 6,561,803; U.S. Pat. No. 6,567,582; U.S. Pat. No. 6,610,053; U.S. Pat. No. 6,616,447; U.S. Pat. No. 6,616,451; U.S. Pat. No. 6,669,685; U.S. Pat. No. 6,744,790 and U.S. Pat. No. 6,821,272.

The above-described embodiments have been provided by way of example, and the present invention is not limited to these examples. For example, some embodiments may employ 3, 6, 8, or another number of pins rather than 2 or 4 as is used in the examples presented herein. Implementation of general-purpose and specific-purpose connectors may be modified so that general-purpose connectors have two pins and specific-purpose connectors have four pins. In this instance, roles of high and low logic states in the CPU (cf. FIG. 4) may be reversed. Other mechanisms of contact between connector and adapter 100 (FIG. 2) or apparatus 300 (FIG. 4) may be employed. For example, magnetic, inductive, radio frequency, or optical methods/devices may be used in some embodiments. The present invention can have applicability in the context of various configurations and components, such as connectors and adapters, for providing discrimination between various types of users, processes, protocols and/or equipment. Although described in the context of a multi-state system for providing discrimination between two states (e.g., general-purpose and specialized equipment), more than two states of various types may be provided in modified embodiments and/or applications (such as applications for providing user, device, process, or system identification). An example of such a modified application can comprise implementation of radio-frequency identification (RFID) implementations in which, for example, RF signals are provided in addition to or as an alternative to the above described pins and pin-contacting surfaces. For example, in embodiments wherein the above-discussed pins and pin-contacting surfaces are omitted, circuitry and/or microprocessors may be used for facilitating communication (e.g., RFID communication using any type of communication protocol, goal, or functionality known to those skilled in the art) between devices and/or users for various purposes including those set forth above and others, such as the discrimination between (e.g., identification of) different users and/or equipment.

As already mentioned, according to other modifications, key 206 and notch 106 implementations may not be required in some embodiments. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention should not be limited by the disclosed embodiments, but is to be defined by reference to the appended claims.

What is claimed is:

1. A method of accepting a fiber connector, the method comprising:
    providing an adapter configurable in both a first and a second configuration, the adapter having an area with three or more conductive surfaces arranged about the area, whereby the adapter is provided in the first configuration having four conductive pin-contacting surfaces circularly arranged in order as northeast, southeast, southwest and northwest;
    coupling one of a first-purpose fiber connector and a second-purpose fiber connector to a point on the adapter;
    accepting the first-purpose fiber connector when coupled to the point but not accepting the second-purpose fiber connector when coupled to the point, when the adapter is configured in the first configuration; and
    accepting the first-purpose fiber connector when coupled to the point and accepting the second-purpose fiber connector when coupled to the point, when the adapter is configured in the second configuration.

2. The method as set forth in claim 1, wherein the accepting of a first-purpose fiber connector comprises accepting a fiber connector having four pins electrically connected together, the four pins being capable of making electrical contact with the four conductive pin-contacting surfaces.

3. The method as set forth in claim 1, further comprising:
    electrically connecting the northwest and the southeast pin-contacting surfaces; and
    electrically connecting the northeast and the southwest pin-contacting surfaces.

4. A method of accepting a fiber connector, the method comprising:
    providing an adapter configurable in both a first and a second configuration, the adapter having an area with three or more conductive surfaces arranged about the area, whereby the adapter is provided in the second configuration having four conductive, pin-contacting, electrically isolated surfaces circularly arranged in order as northeast, southeast, southwest and northwest with the method comprising electrically connecting the northwest and the northeast pin-contacting surfaces and electrically connecting the southeast and the southwest pin-contacting surfaces;
    coupling one of a first-purpose fiber connector and a second-purpose fiber connector to a point on the adapter;
    accepting the first-purpose fiber connector when coupled to the point but not accepting the second-purpose fiber connector when coupled to the point, when the adapter is configured in the first configuration; and
    accepting the first-purpose fiber connector when coupled to the point and accepting the second-purpose fiber connector when coupled to the point, when the adapter is configured in the second configuration.

5. The method as set forth in claim 4, wherein the accepting comprises accepting a second-purpose fiber connector having two pins electrically connected together, the two pins being capable of making electrical contact with one of a northwest-southeast pair of conductive pin-contacting surfaces and a northeast-southwest pair of conductive pin-contacting surfaces.

6. A system for controlling acceptance of a fiber connector of an electromagnetic energy outputting device, the system being provided from a seller to a purchaser with an adapter configurable in both a first and a second configuration according to a decision by the purchaser, the adapter being coupleable to a fiber connector comprising one of a first-purpose fiber connector and a second-purpose fiber connector, the adapter in the first configuration comprising an area with three or more conductive surfaces arranged about the area and being capable of accepting a fiber connector when it is a first-purpose fiber connector coupled to a point of the adapter and rejecting the fiber connector when it is a second-purpose fiber connector coupled to the point, and the adapter in the second configuration being capable of accepting the fiber connector when it is a first-purpose fiber connector coupled to the point and accepting the fiber connector when it is a second-purpose fiber connector coupled to the point, wherein the conductive surfaces comprise four conductive, pin-contacting, electrically isolated surfaces, wherein the northwest and southeast pin-contacting surfaces are electrically connected and wherein the northeast and southwest pin-contacting surfaces are electrically connected.

7. A system for controlling acceptance of a fiber connector of an electromagnetic energy outputting device, the system being provided from a seller to a purchaser with an adapter configurable in both a first and a second configuration according to a decision by the purchaser, the adapter being coupleable to a fiber connector comprising one of a first-purpose fiber connector and a second-purpose fiber connector, the adapter in the first configuration comprising an area with three or more conductive surfaces arranged about the area and being capable of accepting a fiber connector when it is a first-purpose fiber connector coupled to a point of the adapter and rejecting the fiber connector when it is a second-purpose fiber connector coupled to the point, and the adapter in the second configuration being capable of accepting the fiber connector when it is a first-purpose fiber connector coupled to the point and accepting the fiber connector when it is a second-purpose fiber connector coupled to the point, and further comprising a second-purpose fiber connector comprising two pins electrically connected, the two pins being capable of making electrical contact with one of a northwest-southeast pair and a northeast-southwest pair of pin-contacting surfaces, wherein:
 the adapter, when configured in the second configuration, comprises four conductive pin-contacting surfaces circularly arranged in order as northeast, southeast, southwest and northwest;
 the northwest and northeast pin-contacting surfaces are electrically connected; and
 the southeast and southwest pin-contacting surfaces are electrically connected.

8. A method of accepting a fiber connector, the method comprising:
 providing an adapter in a form of a first configuration;
 accepting a first-purpose fiber connector when the adapter is configured in the first configuration;
 providing the adapter in a form of a second configuration, the adapter when configured in the second configuration having four conductive, pin-contacting, electrically isolated surfaces circularly arranged in order as northeast, southeast, southwest and northwest, with the northwest and the northeast pin-contacting surfaces being electrically connected and the southeast and the southwest pin-contacting surfaces being electrically connected; and
 accepting one of a first-purpose fiber connector and a second-purpose fiber connector when the adapter is configured in the second configuration, the acceptance of a second-purpose fiber connector comprising accepting a second-purpose fiber connector having two pins electrically connected together, the two pins being capable of making electrical contact with one of a northwest-southeast pair of conductive pin-contacting surfaces and a northeast-southwest pair of conductive pin-contacting surfaces.

\* \* \* \* \*